(12) United States Patent
Lupien et al.

(10) Patent No.: US 9,011,639 B2
(45) Date of Patent: Apr. 21, 2015

(54) WATERLESS DEGUMMING SYSTEM

(75) Inventors: John C. Lupien, Omaha, NE (US); Michael Dyas, Waterloo, NE (US)

(73) Assignee: Bastlab, LLC, Omaha, NE (US)

( * ) Notice: Subject to any disclaimer, the term of this patent is extended or adjusted under 35 U.S.C. 154(b) by 181 days.

(21) Appl. No.: 13/810,923

(22) PCT Filed: Jul. 21, 2011

(86) PCT No.: PCT/US2011/044826
§ 371 (c)(1),
(2), (4) Date: Mar. 26, 2013

(87) PCT Pub. No.: WO2012/012620
PCT Pub. Date: Jan. 26, 2012

(65) Prior Publication Data
US 2013/0184452 A1  Jul. 18, 2013

Related U.S. Application Data

(60) Provisional application No. 61/366,340, filed on Jul. 21, 2010.

(51) Int. Cl.
*D21B 1/36* (2006.01)
*C07H 1/06* (2006.01)
*D01B 9/00* (2006.01)
*D01C 1/02* (2006.01)

(52) U.S. Cl.
CPC .. *C07H 1/06* (2013.01); *D01B 9/00* (2013.01); *D01C 1/02* (2013.01)

(58) Field of Classification Search
USPC ................... 162/21, 234; 536/56; 422/186.12
See application file for complete search history.

(56) References Cited

U.S. PATENT DOCUMENTS

| | | | | |
|---|---|---|---|---|
| 1,691,903 A | * | 11/1928 | Mortimer | 208/146 |
| 1,814,155 A | * | 7/1931 | Haughey | 162/14 |
| 2,009,944 A | * | 7/1935 | Nordmann | 162/24 |
| 2,931,708 A | * | 4/1960 | Aamot | 75/10.29 |
| 2006/0243323 A1 | | 11/2006 | Wantling et al. | |
| 2007/0181035 A1 | | 8/2007 | Wantling et al. | |
| 2008/0003429 A1 | | 1/2008 | Luo et al. | |
| 2011/0162741 A1 | | 7/2011 | Fink et al. | |

* cited by examiner

*Primary Examiner* — Mark Halpern
(74) *Attorney, Agent, or Firm* — David Milligan; Milligan PC LLO

(57) ABSTRACT

A method and system for cleaning lignin and other gums from lignocellulosic fiber is disclosed. Lignocellulosic fiber is rapidly depressurized to a pressure lower than atmospheric pressure. The fiber is exposed to ionized air during the rapid depressurization. The fiber is then repressurized to a pressure equal to or greater than atmospheric pressure.

6 Claims, 1 Drawing Sheet

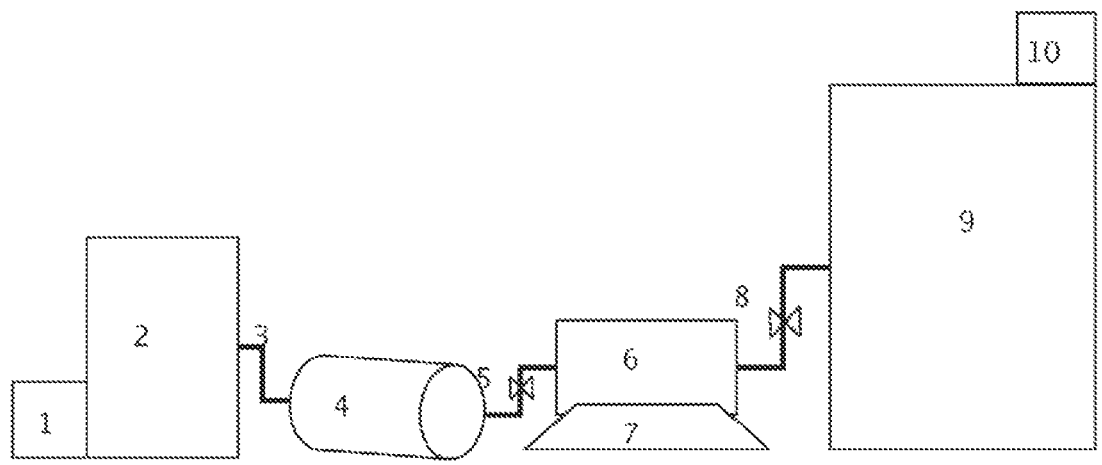

WATERLESS DEGUMMING SYSTEM

This application is a 371 of PCT/US2011/044826 filed 21 Jul. 2011.

CROSS-REFERENCE TO RELATED APPLICATION

The present application claims the benefit under 35 U.S.C. §119(e) of U.S. Provisional Application Ser. No. 61/366,340 filed Jul. 21, 2010, entitled WATERLESS DEGUMMING SYSTEM, which is herein incorporated by reference in its entirety.

FIELD OF INVENTION

The present invention relates to a method of degumming bast fibers for textile applications and to a method of pretreating lignocellulosic fiber for the production of biofuels or chemical feedstock, by the following means: rapid depressurization to vacuum and repressurization atmospheric or greater pressure; rapid temperature fluctuation; and ionic cleaning. The method described in this invention minimizes fiber damage, increases throughput potential, and reduces processing times.

BACKGROUND

In the past, U.S. Pat. No. 2,099,944 described a process of treating bast fiber plants to obtain clean cellulose fiber, lignin, and other gums, comprised of the following steps: 1) warm air drying; 2) rapid temperature reduction; and, 3) prolonged exposure to chilled ionized air. Ozone naturally attacks the carbon bonds of the lignin and nitrous oxide helps remove the pectins and other gums.

The process described is similar to modern ozonolysis systems, which are designed for pretreatment of lignocellulosic materials in order to remove lignin and facilitate enzymatic digestion of the carbohydrates into biofuels. Modern ozonolysis systems expose lignocellulosic materials within a reaction chamber at room temperature and atmospheric pressure to gaseous ozone for a prolonged period of time.

Rapid depressurization to vacuum and repressurization to atmospheric pressure or greater within a vacuum chamber or any suitable pressure vessel has never been contemplated for the purpose of degumming bast fiber. Vacuum rapidly dries and opens the fibrous material. Vacuum also aids in the penetration and diffusion of ionized air within the fibrous material upon repressurization.

U.S. Pat. No. 5,207,870 contemplates the use of vacuum to pretreat wood chips, however the process does not employ rapid pressure swings and the wood chips are in chemical liquid solution not ionized air.

U.S. Pat. No. 5,344,462 discusses the treatment of cellulose, textile fibers, and polymer films by exposure to low pressure plasma discharge. This process does not contemplate rapid pressure swings and it is designed for surface modification of the treated materials, not degumming for textile applications or pretreatment for biofuels production.

SUMMARY OF THE INVENTION

A first objective of this invention is to provide an improved waterless means of rapidly removing lignin and other gums from cellulosic fiber for the purpose of producing a variety of grades of textile fiber and for the pretreatment of ligrocellulosic fiber for biofuels or chemical feedstock production.

A second objective of this invention is to reduce the amount of energy and time required to remove the lignin and other gums from cellulosic fiber.

A third objective of this invention is to improve the quality control of the processed materials and to increase the throughput potential.

A fourth objective of this invention is to provide a means of immediately processing freshly harvested and decorticated bast fibers.

BRIEF DESCRIPTION OF THE DRAWINGS

FIG. 1 is a schematic view of a waterless degumming system.

DETAILED DESCRIPTION

The following example describes a processing system capable of achieving the following actions: rapid depressurization to vacuum and repressurization to atmospheric or greater pressure; rapid temperature fluctuation: and ionic cleaning. The result of these actions separates lignocellulosic fiber into its various molecular components: cellulose, hemicelluloses, and lignin.

The system is consists of an ionic generator with fan 1 attached to ion reservoir 2. The ionic generator 1 blows charged or ionized air into the reservoir 2, which is attached to temperature manipulation vessel 4 by pipe 3. Temperature manipulation vessel 4 is capable of heating of chilling the ionized air by means of coils within the vessel. Pipe 5 runs between temperature manipulation vessel 4 and vacuum reaction chamber 6, which is supported by structural stand 7. Pipe 5 is equipped with a valve. Reaction chamber 6 is attached to vacuum draw down tank 9 by pipe 8 with valve. Vacuum in vacuum draw down chamber 9 is pulled by vacuum pump 10.

The system is operated in the following manner. First, ionic generator 1 is started building concentrated reserved in ion reservoir 2 and temperature manipulation vessel 4. At the same time vacuum pump 10 is switched on to draw down vacuum tank 9. The valves on pipes 5 and 8 are closed in order to concentrate the ions in ion reservoir 2 and create the vacuum within the vacuum draw down tank 9.

Next, lignocelfulosic fiber is placed in reaction chamber 6. The material is exposed to heat and mechanical rotation by common art. When vacuum is achieved in draw down tank 9 the valve on pipe 8 is opened rapidly creating a vacuum in reaction chamber 6. Once vacuum is achieved in reaction chamber 6 the valve on pipe 8 is closed. The vacuum is maintained in reaction chamber 6.

The rapid depressurization shocks the lignocellulosic fiber causing it to swell. The vacuum accelerates the drying process.

Next, the valve on pipe 5 is opened allowing the ionized air from ionic reservoir 2 and temperature manipulation vessel 4 to rapidly repressurize reaction chamber 6. A secondary valve or pipe 8 may be opened allowing the ionized air to gradually flow through the reaction chamber for a period of time.

The vacuum and repressurization process facilitates the diffusion and penetration of the ionized air into the lignocellulosic fiber.

The ionized air may either be chilled or heated depending on the processing parameters. Heating and chilling is controlled in temperature manipulation vessel 4.

Heated air helps the transfer of ions arid facilitates the cleaning of the cellulose fiber. A rapid temperature drop through exposure to chilled air cracks the gums that surround the cellulose fiber making it more accessible to the cleaning action of the ionized air.

The general process described in this invention may be repeated as many times as is necessary to achieve the desired degree of processing.

When the process is completed cellulose fiber, lignin, and the various gums may be collected through a variety of methods that are commonly known. Recovered cellulose fiber may be utilized for textile applications. Or, the carbohydrate portion, the cellulose and hennicelluloses, may be subjected to further treatment for biofuels production.

It will be understood that the previous example serves to illustrate one possible means of achieving the actions and objectives of this invention.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that relative terms are intended to encompass different orientations of the device in addition to the orientation depicted in the Figures.

Moreover, it will be understood that although the terms first and second are used herein to describe various features, elements, regions, layers and/or sections, these features, elements, regions, layers and/or sections should not be limited by these terms. These terms are only used to distinguish one feature, element, region, layer or section from another feature, element, region, layer or section. Thus, a first feature, element, region, layer or section discussed below could be termed a second feature, element, region, layer or section, and similarly, a second without departing from the teachings of the present invention.

It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Further, as used herein the term "plurality" refers to at least two elements. Additionally, like numbers refer to like elements throughout.

Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow. The scope of the disclosure is not intended to be limited to the embodiments shown herein, but is to be accorded the full scope consistent with the claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims.

What is claimed is:

1. A method of stabilizing and cleaning lignocellulosic fiber comprising the steps of rapid depressurizing of the fiber to a pressure lower than atmospheric; and rapid repressurizing of the fiber to atmospheric pressure or greater.

2. The method of claim 1, wherein the fiber is exposed to variation in temperature as it is either depressurized or repressurized.

3. The method of claim 2, further comprising exposing the fiber to ionized air during the step of rapid depressurization.

4. The method of claim 1, further comprising exposing the fiber to ozone.

5. A method of cleaning lignin and other gums from lignocellulosic fiber comprising the steps of:
   rapid depressurizing of the fiber to a pressure rower than atmospheric;
   exposing said fiber to ionized air during the step of rapid depressurization to vacuum; and
   rapid repressurizing of the fiber to atmospheric pressure or greater.

6. The method of claim 5, further comprising the step of exposing the fiber to a variation in temperature.

\* \* \* \* \*